United States Patent [19]

Graeff et al.

[11] Patent Number: 4,736,398
[45] Date of Patent: Apr. 5, 1988

[54] APPARATUS FOR THE DIGITAL SUBTRACTION ANGIOGRAPHY IN ENERGY SUBTRACTION MODE

[75] Inventors: Walter Graeff, Appen; Wolf-Rainer Dix; Claus-Christian Glüer, both of Hamburg, all of Fed. Rep. of Germany

[73] Assignee: Deutsches Elektronen-Synchrotron Desy, Hamburg, Fed. Rep. of Germany

[21] Appl. No.: 860,885

[22] Filed: May 8, 1986

[30] Foreign Application Priority Data

May 11, 1985 [DE]  Fed. Rep. of Germany ....... 3517101

[51] Int. Cl.⁴ .............................................. H05G 1/64
[52] U.S. Cl. ........................................ 378/99; 378/98; 378/84
[58] Field of Search ...................... 378/99, 84, 85, 82, 378/5, 98; 250/361 R, 363 R, 367

[56] References Cited

U.S. PATENT DOCUMENTS

| | | | |
|---|---|---|---|
| 3,160,749 | 12/1964 | Spielberg | 378/85 |
| 4,146,794 | 3/1979 | Duinker | 378/7 |
| 4,179,100 | 12/1979 | Sashin et al. | 378/99 |
| 4,445,226 | 4/1984 | Brody | 378/84 |
| 4,626,688 | 12/1986 | Barnes | 378/156 |

OTHER PUBLICATIONS

Thieberger et al., "Multiple Event 2D Image Intersifier Scintillation Detector", Nuclear Instruments and Methods, 1987, (1981), pp. 611–614.
Zeman et al., "Evaluation of Synchrontron S-Rays for Transvenous Coronary Angiography", Nuclear Instruments and Methods in Physics Research, 222, (1984), pp. 308–318.

*Primary Examiner*—Janice A. Howell
*Assistant Examiner*—David P. Porta
*Attorney, Agent, or Firm*—Cushman, Darby & Cushman

[57] ABSTRACT

The invention relates to an apparatus for the digital subtraction angiography in the energy subtraction mode, in which simultaneously two images with monochromatic X-radiation are recorded. One image is recorded with a monochromatic X-ray of energy $E_1$ and a second image with a further monochromatic X-ray $E_2$. The X-rays are converted into visible light by a scintilator (2). This light is recorded in linear manner in a detector (3). A computer subtracts the images obtained in linear manner in this way, so that an image can be produced, which clearly reproduces an organ or its vessels if the same is previously filled with an iodine contrasting agent. It is merely necessary for the energy of ray $E_1$ to be just below and that of the other ray $E_2$ just above the iodine absorption edge of 33 keV.

14 Claims, 4 Drawing Sheets

APPARATUS FOR THE DIGITAL SUBTRACTION ANGIOGRAPHY IN ENERGY SUBTRACTION MODE

BACKGROUND OF THE INVENTION

The invention relates to an apparatus for digital subtraction angiography in the energy subtraction mode with a monochromator for producing two monochromatic X-rays of different energy, with a detector arranged in the optical path of the X-rays behind the monochromator and with a control circuit.

Such an apparatus is already known from Nuclear Instruments and Methods in Physics Research 222, 1984, pp 308–318, North Holland Publishing Company, Amsterdam. It is used for investigating the moving organs of a patient on which an abnormality is assumed. An example is the investigation of the heart to establish whether there is a likelihood of an acute closure of a coronary due to a blood clot. For this purpose an iodine contrasting agent is injected into a vein of the patient's arm and the patient is successively irradiated in linear manner with two linear collimated X-rays, whereof one has an energy $E_1$ just below the iodine absorption edge of 33 keV and the other an energy $E_2$ just above the iodine absorption edge. The two X-rays are alternately let through to the same point of the detector through time-controllable beam closures. As the absorption of the X-rays by iodine above the absorption edge is six times as great as below it, but the absorption by the tissue and bones remains the same, there is a clear iodine contrast on subtracting from the first image obtained with energy $E_2$ from the second image obtained with the energy $E_1$. However, for this purpose a very intense X-radiation is required, which can e.g. be obtained as synchroton radiation on high energy accelerators or storage rings, such as at DESY or SLAC in Stanford.

A disadvantage of the known apparatus is that it is necessary to have rapidly moving parts for the beam closure in order to release the X-ray and as a result of the necessary down times, the patient cannot be continuously imaged at beam reversal.

OBJECTS AND SUMMARY OF THE INVENTION

The problem of the present invention is to provide a mechanically simplified apparatus for digital subtraction angiography (DSA) in the energy subtraction mode, which avoids the aforementioned disadvantages and permits a substantially continuous imaging of the patient.

This problem is solved by the apparatus of the aforementioned type, which is characterized in that the detector has two, parallel, spaced scintillator rows, at least one image intensifier and at least one photodiode row, that on the output side the image intensifier is connected via first glass fibre bundles to the scintillator rows and the output side via second glass fibre bundles to at least one photodiode row and that the first and second glass fibre bundles in each case pass from a linear, juxtaposed arrangement into a circular arrangement filling the entrance or exit window of the at least one image intensifier.

As a result of the simultaneous irradiation with two X-rays, the apparatus operates faster by a factor of 2, because there are no reversing times. As a result of the inventive coupling of the glass fibre bundles to the scintillator row there is a true shape or cross-sectional conversion or transformation, without there being any cross-sectional change of the individual fibres, so that a light loss is prevented. Cross-sectional conversion takes place is such a way that at the input side of the image intensifier there is a conversion of two juxtaposed rows into a circular surface and at the output side of the image intensifier from a circular surface into a single row, which can be split up over one or more linear photodiode components. This initially only represents a change to the position of the glass fibre bundles for the optimum utilization of the image intensifier. However, on the output side of the image intensifier, the individual glass fibre bundles undergo a further cross-sectional conversion, in that individual fibres thereof having a diameter of 30 $\mu$m are combined at the exit window of the image intensifier to bundles having a roughly circular cross-section with a diameter of 0.7 mm and comprising in each case roughly 200 to 250 fibres. However, at the photodiode row they are combined to a rectangular cross-section of 100 $\mu$m wide and 2.5 mm high, in order to bring about optimum utilization of the photodiode row.

BRIEF DESCRIPTION OF THE DRAWINGS

The invention is described in greater detail hereinafter relative to non-limitative embodiments and the attached drawings, which show.

DETAILED DESCRIPTION

Figure 1:
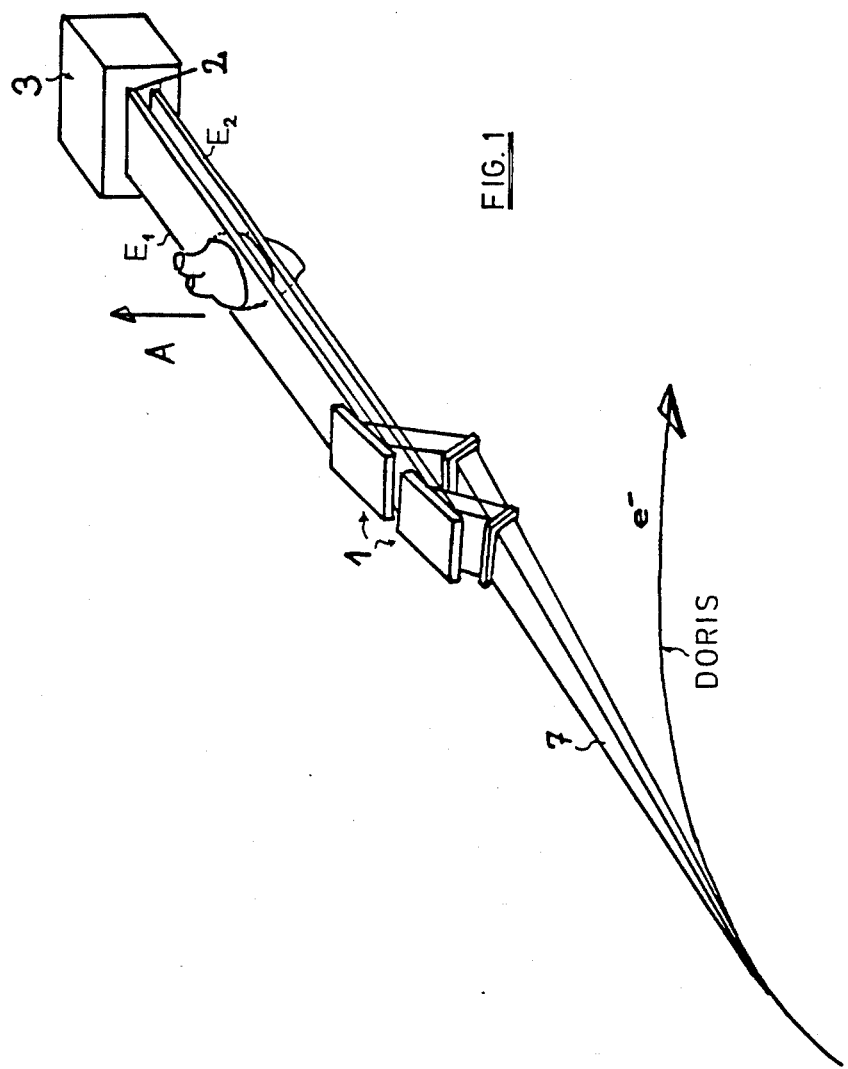
FIG. 1 is a diagrammatic arrangement of the apparatus in the optical path of a synchroton.
Figure 2:
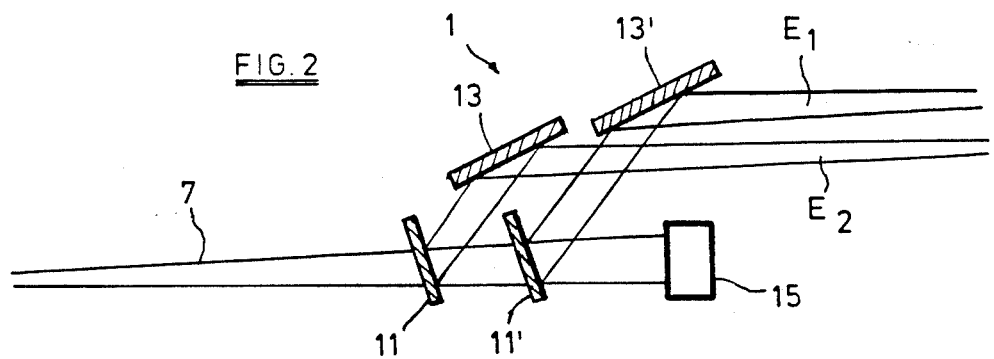
FIG. 2 is a double crystal monochromator of the apparatus of FIG. 1.

FIG. 1 shows as the X-ray source the storage ring DORIS in diagrammatic representation and from which the synchrotron radiation is irradiated in the form of a frequency mix and therefore as a so-called polychromatic or "white" beam 7, which is passed through a system of collimators and diaphragms (not shown) to a monochromator 1, shown in detail in FIG. 2. In the case of DORIS, monochromator 1 is roughly 30 to 35 meters from the source point of the radiation. In the vicinity of its source point in DORIS, the white beam 7 has a roughly elliptical beam cross-section, whose minor axis is roughly 2 mm long, whilst the length of the horizontal major axis is approximately 4 mm. Monochromator 1 is advantageously set up half way between the source point and a detector 3. By beam shutters and natural divergence, at the location of monochromator 1 the beam has a horizontal width of approximately 60 mm and a height of approximately 5 mm. Through the use of a double crystal monochromator 1, there are two monoenergy beams with an energy of $E_1$ and $E_2$, which strike scintillator rows 2, 2' at the entrance or input of detector 3. There they have a spacing of 1.5 mm and a horizontal width of 120 mm and a height of 0.5 mm. Upstream of the scintillator rows 2, 2' is located in the operating state the object to be investigated, e.g. a patient or more precisely the heart, indicated diagrammatically in FIG. 1. It is also possible to see a movement of the heart in the vertical direction, as indicated by an arrow A. This movement is achieved by a chair (not shown) on which the person sits. The chair can be moved up and down in a controlled manner, control being provided by a control circuit (not shown) 5. According to one embodiment the chair performs an upward movement of approximately 40 cm, whereby the first 10 cm serve to accelerate the chair and the person sitting on it, the following 20 cm a path for movement with constant speed of 60 cm/s, and the final 10 cm for slowing down purposes. Thus, the organ of the patient to be investigated, e.g. the heart, is moved during roughly 200 msc through the two monochromatic beams $E_1$ and $E_2$. The same investigation point is so rapidly successively imaged by beams $E_1$ and $E_2$ that the two beam images can readily be subtracted.

FIG. 2 shows a double crystal monochromator 1, in which the white beam 7 strikes two Laue crystals 11, 11' arranged successively in the path of the white beam 7 and is collected in an absorber 15 in the extension thereof. The first Laue crystal 11 selects a first energy $E_1$ according to Bragg's equation, which is deflected from a first Bragg's crystal 13 as a monochromatic X-ray $E_1$. The second Laue crystal 11' selects a second energy $E_2$ and this X-ray is deflected from a second Bragg's crystal 13' as an X-ray of energy $E_2$. In this way the monochromatic X-ray shown in FIG. 1 and having the energies $E_1$ and $E_2$ are derived from a polychromatic or white beam 7. In one construction, the Laue crystals 11, 11' are e.g. Si-111 crystals. In this case Ge-111 crystals are used as the Bragg crystals 13, 13'. The use of Laue crystals 11, 11' in conjunction with Bragg crystals 13, 13' permits a vertical beam focussing.

Figure 3:
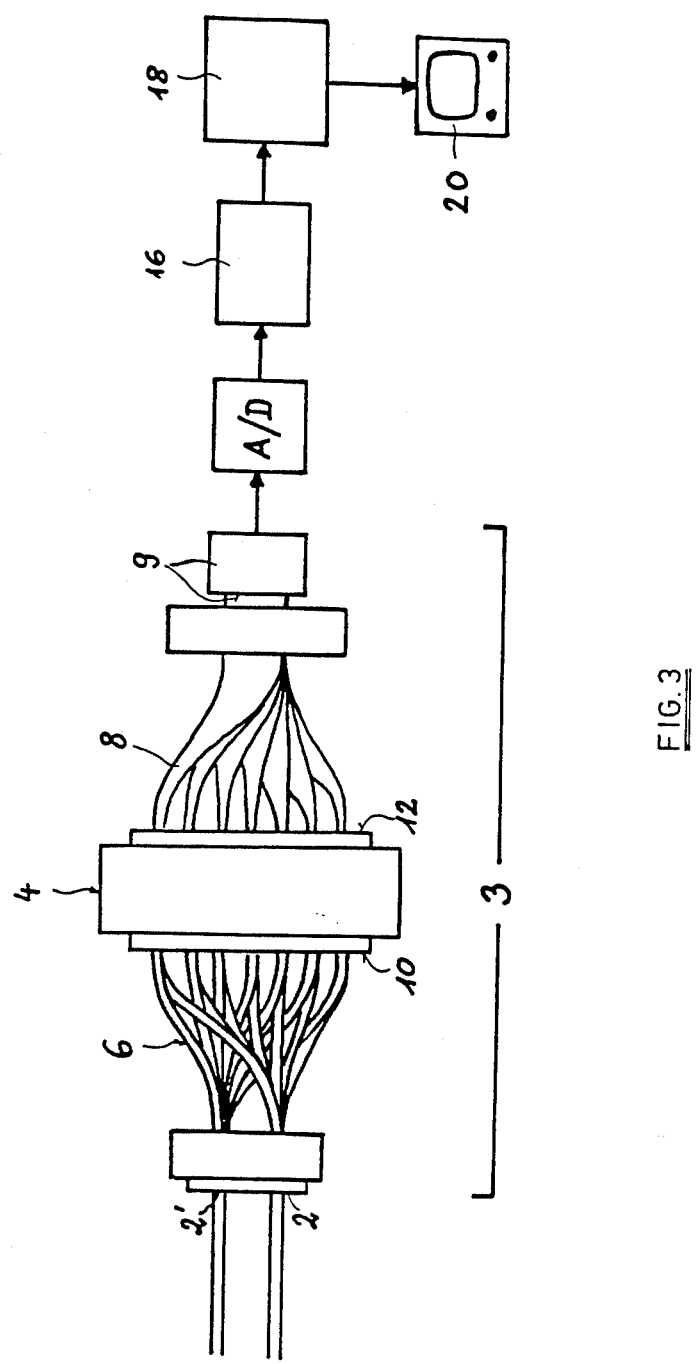
FIG. 3 is a diagrammatic block circuit diagram of the detector of the apparatus of FIG. 1.

After the two monochromatic beams $E_1$ and $E_2$ have passed through a patient's heart, another member or any other object, they strike the scintillator rows 2, 2' shown in FIG. 3. In this embodiment, the scintillator rows 2, 2' in each case comprise a luminous pigment, e.g. of type 53046 of Riedel-de Haen AG, which is marketed under the name LUMILUX Grün RGS or Grün RGS-10. Scintillator rows 2, 2' are sedimented on to the end face of a light conductor, in the form of a powder layer with a thickness of roughly 200 to 300 $\mu$m. In one construction they are split up in each case into 255 image elements of $0.5 \times 0.5$ mm$^2$ cross-section, in that they are each coupled to 255 glass fibre bundles 6, which are combined and surface ground in a mount at one end. In another embodiment the scintillator material is placed in small boxes, which in each case extend over the area of the upper and lower X-ray $E_1$ and $E_2$, so that one box in each case detects one image element from two X-rays. There is an insulation with respect to the adjacent boxes, so that there is no cross-talk or interference. In the vicinity of the upper and lower X-rays, there is in each case a first glass fibre bundle 6. In another embodiment the scintillator is applied as a crystal, individual zones being defined by sawing and aluminizing the sections, as is described e.g. in DE-OS No. 31 40 145.

Figure 4:
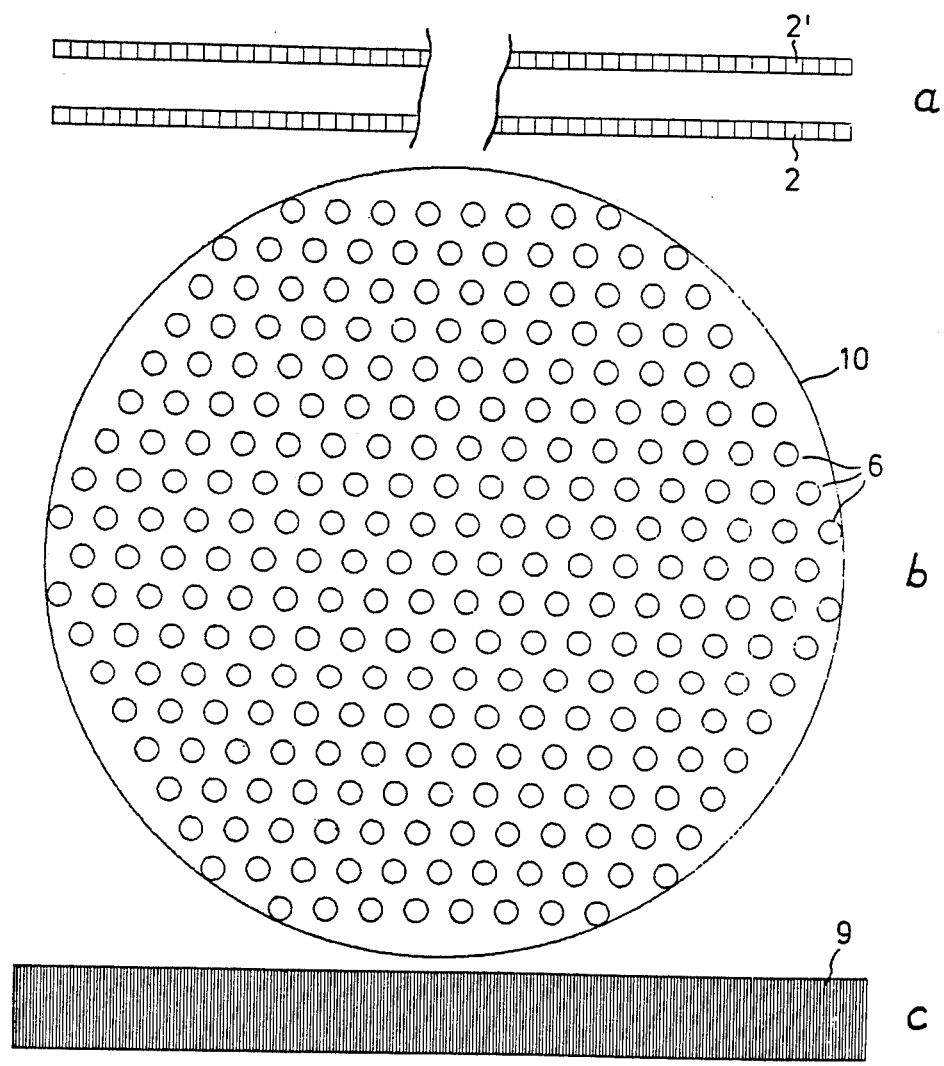
FIG. 4 shows the glass fibre bundle cross-sectional conversion and the arrangement thereof in the detector of the apparatus according to FIG. 1.

It is essential for the invention that the first $2 \times 255$ glass fibre bundles 6, which emanate from two superimposed scintillator rows 2, 2', as shown in FIGS. 3 and 4a, are so guided on the entrance window 10 of an image intensifier 4, that they have the maximum distance from one another. This is advantageously achieved through a hexagonal pattern, as shown in FIG. 4b. In the case of a circular image intensifier surface with a diameter of 25 mm and the use of only one image intensifier, all the bundles have a center-to-center spacing of 0.97 mm. In another construction, the glass fibres bundles are uniformly distributed over two image intensifiers, so that a center-to-center distance of 1.36 mm and consequently an even further reduced cross-talk of the image information in the image intensifier is achieved. Thus, there is an optimum utilization of the available entrance face of the image intensifier.

The image intensifiers 4 can only be intensifiers which image in a distortion-free manner and generally only proximity focussing image intensifiers. In the construction according to FIG. 3, use is made of an image intensifier 4 supplied by Proxitronic with a 100× intensification and a resolution of 30 line pairs/mm. From the exit window 12 of image intensifier 4, the light is passed via $2 \times 255$ second glass fibre bundles 8 to a photodiode row 9. It is important when coupling the second glass fibre bundle 8 to the exit window 12 that the configuration of the second glass fibre bundle 8 corresponds to the configuration of the first glass fibre bundle 6 at entrance window 10. This is achieved in that the glass fibre bundles 6, 8 are individually threaded through a mounting support with the pattern according to FIG. 4b and are cut in the plane of the mounting support, so that then the first and second glass fibre bundles 6, 8 respectively are formed. In one construction, the mounting support comprises two identical, superimposed metal plates with the hole pattern according to FIG. 4b. For separating the glass fibre bundles, the two metal plates are drawn apart to a distance of approximately 0.5 cm after threading through the bundles 6, 8. The latter are film-coated, so that the pattern according to FIG. 4b is retained and then separation takes place between the plates. After grinding the sections, they are coupled on image intensifier 4 at the entrance window 10 or exit window 12 with a translucent immersion oil or by bonding. In another construction the mounting support comprises a plexiglass plate with a hole pattern according to FIG. 4b. Following threading through and film-coating of the glass fibre bundles 6, 8, the plexiglass plate is cut through at right angles to bundles 6, 8, and the sections are ground and coupled to image intensifier 4 in the aforementioned manner. The second glass fibre bundles 8 are combined into rows behind the image intensifier 4, the cross-section of each glass fibre bundle 8 being converted or transformed in such a way that it precisely corresponds to the surface of one or more photodiodes of row 9. Thus, with respect to the cross-section of the first glass fibre bundles 6 there is a true cross-sectional transformation at the location of the scintillator without it being necessary to modify the cross-section of the individual fibres. This leads to maximum transmission and optimum illumination of the photodiodes. The second glass fibre bundles 8 are coupled to the photodiode row 9, in that they are e.g. bonded thereto or brought into close contact with a translucent immersion oil, which minimizes reflection losses of light. The photodiode row 9 e.g. contains 255 image elements with $0.1 \times 2.5$ mm$^2$, as in FIG. 4c, the light of each image element of the second glass fibre bundle 8 and therefore also the first glass fibre bundle 6 illuminating four photodiodes. The 256th image element is used for standardizing to a constant input intensity and is also transferred by image intensifier 4. In one construction, use was made of two photodiode rows called RETICON RL1024SF. The output signals of the photodiodes are converted by an analog-digital converter into digital signals and fed into a buffer store 16, which is used for forming a buffer between a following computer 18 and the detector 3, because the latter supplies data more rapidly than they can be stored by the computer 18. In per se a known manner, the computer 18 then controls the image evaluation, in that it subtracts an image of energy $E_1$ from a second image of energy $E_2$ and the image obtained is shown on a monitor 20. In addition, the computer 18 is responsible for the control of the complete apparatus and for moving the object or body part to be investigated through the two X-rays $E_1$ and $E_2$, for adjusting the monochromator 1, for the read out of data from detector 3 and for the coordination of the complete apparatus with medical equipment, such as an ECG.

It is obvious that the invention is not limited to the use in the medical field and can be used everywhere where it is necessary to take instantaneous exposures with X-rays of rapidly moving objects without there being damage from the outside.

We claim:

1. Apparatus for digital subtraction angiography in an energy subtraction mode comprising a monochromator for producing two monochromatic X-rays of different energies ($E_1$, $E_2$), a detector arranged behind the monochromator in the path of the X-ray, said detector having two parallel, spaced scintillator rows each of the two scintillator rows receiving one of the two X-ray beams of differing energy for the simultaneous detection of the two X-ray beams, at least one image intensifier and at least one photodiode row said image intensifier being connected on an input via a first glass fiber bundle to the scintillator rows and connected on an output side via second glass fibre bundles to the at least one photodiode row, said first and second glass fiber bundles in each case passing from a linear, juxtaposed arrangement into a circular arrangement filling the entrance and exit windows of the at least one image intensifier in which arrangement the individual glass fiber bundles have maximum distance from one another.

2. Apparatus according to claim 1, wherein the two scintillator rows are arranged in a spacing within the range of 0.5 to 100 mm, each of the two rows being subject to the action of an X-ray energy $E_1$ or $E_2$.

3. Apparatus according to claim 1, wherein the two scintillator rows are arranged in a spacing within the range of 0.5 to 10 mm, each of the two rows being subject to the action of an X-ray energy $E_1$ or $E_2$.

4. Apparatus according to claim 1, wherein the two scintillator rows are arranged in a spacing within the range of 1 to 4 mm, each of the two rows being subject to the action of an X-ray energy $E_1$ or $E_2$.

5. Apparatus according to claim 1 or 2 wherein the scintillator rows have a length falling in the range 20 to 500 mm, and have a height falling in the range of 0.1 to 3 mm.

6. Apparatus according to claim 1 or 2 wherein the scintillator rows have a length of 120 mm and a height of 0.5 mm.

7. Apparatus according to claim 1 wherein the image intensifier is a distortion-free-imaging image intensifier with proximity focussing.

8. Apparatus according to claim 1, wherein said monochromator includes means for producing one monochromatic X-ray beam at an energy slightly below the K edge of a contrast material and for producing another monochromatic X-ray beam at an energy slightly above the K edge of the contrast material.

9. Apparatus according to claim 8, wherein the two scintillator rows are arranged in a spacing within the range of 0.5 to 100 mm, each of the two rows being subject to the action of an X-ray energy $E_1$ or $E_2$.

10. Apparatus according to claim 8, wherein the two scintillator rows are arranged in a spacing within the range of 0.5 to 10 mm, each of the two rows being subject to the action of an X-ray energy $E_1$, or $E_2$.

11. Apparatus according to claim 8, wherein the two scintillator rows are arranged in a spacing within the range of 1 to 4 mm, each of the two rows being subject to the action of X-ray energy $E_1$ or $E_2$.

12. Apparatus according to claim 8 wherein the scintillator rows have a length falling in the range 20 to 500 mm, and have a height falling in the range of 0.1 to 3 mm.

13. Apparatus according to claim 8 wherein the scintillator rows have a length of 120 mm and a height of 0.5 mm.

14. Apparatus according to claim 8 wherein the image intensifier is a distortion-free-imaging image intensifier with proximity focussing.

* * * * *